United States Patent
Wenzel et al.

(10) Patent No.: US 11,247,070 B2
(45) Date of Patent: Feb. 15, 2022

(54) BRACHYTHERAPY TREATMENT PLANNING SYSTEM

(71) Applicant: KONINKLIJKE PHILIPS N.V., Eindhoven (NL)

(72) Inventors: Fabian Wenzel, Hamburg (DE); Thomas Heiko Stehle, Hamburg (DE); Heinrich Schulz, Hamburg (NL); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/962,899

(22) PCT Filed: Mar. 13, 2019

(86) PCT No.: PCT/EP2019/056198
§ 371 (c)(1),
(2) Date: Jul. 17, 2020

(87) PCT Pub. No.: WO2019/179832
PCT Pub. Date: Sep. 26, 2019

(65) Prior Publication Data
US 2021/0244968 A1 Aug. 12, 2021

Related U.S. Application Data
(60) Provisional application No. 62/646,164, filed on Mar. 21, 2018.

(30) Foreign Application Priority Data
Mar. 30, 2018 (EP) ..................................... 18165290

(51) Int. Cl.
*A61N 5/10* (2006.01)
*G06T 7/11* (2017.01)
(Continued)

(52) U.S. Cl.
CPC ........... *A61N 5/103* (2013.01); *A61N 5/1007* (2013.01); *A61N 5/1039* (2013.01); *G06T 7/11* (2017.01);
(Continued)

(58) Field of Classification Search
CPC .... A61N 5/1007; A61N 5/103; A61N 5/1039; A61N 2005/1024; A61N 2005/1025;
(Continued)

(56) References Cited

U.S. PATENT DOCUMENTS 6,360,116 B1 * 3/2002 Jackson, Jr. ......... A61N 5/1027
600/427
6,610,013 B1 * 8/2003 Fenster .................. A61N 5/103
600/439

(Continued)

FOREIGN PATENT DOCUMENTS

CN 104548372 A 4/2015
CN 105825073 A 8/2016
(Continued)

OTHER PUBLICATIONS

Polo et al., "Review of intraoperative imaging and planning techniques in permanent seed prostate brachytherapy", Radiotherapy and Oncology, 94, 2010, pp. 12-23 (Year: 2010).*
(Continued)

*Primary Examiner* — Nay A Maung
*Assistant Examiner* — Jose M Torres
(74) *Attorney, Agent, or Firm* — Sherry Austin (57) ABSTRACT

A brachytherapy treatment planning system includes a processor that: receives a planning image corresponding to at least a portion of a prostate; generates a brachytherapy treatment plan comprising, for each of a plurality of brachytherapy seeds or catheters, a corresponding brachytherapy seed or catheter position in the planning
(Continued)

image such that the plurality of brachytherapy seed or catheter positions in the planning image together satisfy a desired radioactive dose objective in the prostate; receives a pre-treatment image corresponding to the at least a portion of a prostate; and maps each brachytherapy seed or catheter position in the planning image to a corresponding position in the pre-treatment image by performing a registration between the planning image and the pre-treatment image.

20 Claims, 2 Drawing Sheets

(51) Int. Cl.
| | |
|---|---|
| *G06T 7/30* | (2017.01) |
| *G06T 7/149* | (2017.01) |
| *G16H 20/40* | (2018.01) |
| *G16H 30/20* | (2018.01) |
| *G16H 50/30* | (2018.01) |
| *G16H 30/40* | (2018.01) |

(52) U.S. Cl.
CPC .............. *G06T 7/149* (2017.01); *G06T 7/30* (2017.01); *G16H 20/40* (2018.01); *G16H 30/20* (2018.01); *G16H 30/40* (2018.01); *G16H 50/30* (2018.01); *A61N 2005/1024* (2013.01); *A61N 2005/1025* (2013.01); *G06T 2207/10081* (2013.01); *G06T 2207/10088* (2013.01); *G06T 2207/10116* (2013.01); *G06T 2207/10132* (2013.01); *G06T 2207/30081* (2013.01)

(58) Field of Classification Search
CPC ... G06T 7/11; G06T 7/30; G06T 7/149; G06T 2207/10081; G06T 2207/10088; G06T 2207/10116; G06T 2207/10132; G06T 2207/30081; G16H 20/40; G16H 30/20; G16H 30/40; G16H 50/30
See application file for complete search history.

(56) References Cited

U.S. PATENT DOCUMENTS

| | | | |
|---|---|---|---|
| 8,908,940 B1* | 12/2014 | Piper | G06T 3/60 |
| | | | 382/128 |
| 10,426,974 B2 | 10/2019 | Amthor | |
| 2003/0065260 A1 | 4/2003 | Cheng | |
| 2003/0130573 A1* | 7/2003 | Yu | A61N 5/103 |
| | | | 600/407 |
| 2004/0225174 A1 | 11/2004 | Fuller | |
| 2009/0014015 A1 | 1/2009 | Tutar | |
| 2014/0206926 A1* | 7/2014 | van der Laarse | A61N 5/1031 |
| | | | 600/8 |
| 2014/0303423 A1* | 10/2014 | Amthor | A61N 5/1027 |
| | | | 600/8 |
| 2015/0141733 A1* | 5/2015 | Kumar | A61N 5/1031 |
| | | | 600/1 |
| 2015/0306426 A1* | 10/2015 | Marvast | A61N 5/1048 |
| | | | 600/424 |
| 2017/0301088 A1* | 10/2017 | Bharat | A61B 34/20 |
| 2019/0046813 A1* | 2/2019 | Zhou | G16H 50/70 |

FOREIGN PATENT DOCUMENTS

| | | |
|---|---|---|
| EP | 2535086 A1 | 12/2012 |
| EP | 3264298 A1 | 3/2018 |
| WO | 2012001551 A1 | 1/2012 |
| WO | WO2016092463 A1 | 6/2016 |
| WO | WO2016196973 A1 | 12/2016 |

OTHER PUBLICATIONS

PCT International Search Report, International application No. PCT/EP2019/056198, dated Jun. 14, 2019.
Lee D.C. et al., "Recent Developments and Best Practice in Brachytherapy Treatment Planning", Br Journal of Radiology, vol. 87, issue 1041, 2014.
Papagiannis P. et al., "Current State of the Art Brachytherapy Treatment Planning Dosimetry Algorithms", Br Journal of Radiology, vol. 87, issue 1041, 2014.

* cited by examiner

BRACHYTHERAPY TREATMENT PLANNING SYSTEM

CROSS-REFERENCE TO RELATED APPLICATIONS

This patent application claims the priority benefit under 35 U.S.C. § 371 of International Patent Application no. PCT/EP2019/056198 filed Mar. 13, 2019, which claims the benefit of European Patent Application No. EP18165290.0, filed on Mar. 30, 2018 and which claims the benefit of U.S. Application Ser. No. 62/646,164, filed on Mar. 21, 2018. These applications are hereby incorporated by reference herein in their entirety.

FIELD OF THE INVENTION

The invention relates to a brachytherapy treatment planning system. A related method and computer program product are also disclosed.

BACKGROUND OF THE INVENTION

Brachytherapy is commonly indicated for the treatment of prostate cancer. Either low dose rate, i.e. LDR, or high dose rate, i.e. HDR brachytherapy may be indicated. LDR brachytherapy is typically indicated for patients with low or intermediate risk prostate cancer. In LDR brachytherapy, radioactive seeds are permanently implanted into the prostate to destroy nearby tumor cells. After an initial outpatient appointment to determine the suitability of LDR brachytherapy, the patient typically undergoes an imaging procedure, for example using magnetic resonance imaging, i.e. MRI, or computed tomography, i.e. CT, to determine the exact shape and size of the prostate. A treatment plan that provides a desired radioactive dose distribution in the prostate is subsequently generated in accordance with this 'treatment planning' image. During a subsequent visit to the treatment center, around 100 radioactive seeds that typically include radioactive iodine ($^{125}$I) are implanted under general anesthetic in predetermined positions in the prostate in accordance with the treatment plan. Some 20-30 needles each implant between 2 and 6 seeds, typically with the support of a mechanical grid-like device known as a template. One or more 'intra-treatment' images may be made during the implantation procedure to verify the positioning of the needles and the seeds respective the anatomy. Intra-treatment images are conventionally made using X-ray, CT, or ultrasound. After the implantation, a 'post-treatment' CT image is sometimes made in order to verify the seed implant positions and thereby confirm that the desired radioactive dose distribution will be achieved. The radioactivity of the LDR seeds diminishes over time, becoming negligible after around 10 months.

HDR brachytherapy by contrast involves the temporary insertion of radioactive beads into the prostate, typically via plastic rods, i.e. catheters. HDR brachytherapy is suited for both early stage and some locally-advanced prostate cancers. For example it is ideally suited to patients with high risk prostate cancer that has spread to the seminal vesicles. As with LDR brachytherapy, HDR brachytherapy patients typically undergo a similar initial outpatient appointment, following which an imaging procedure is used to generate a planning image and subsequently a treatment plan. During a subsequent visit to the treatment center some 15 to 20 catheters are inserted into the prostate, through each of which a radioactive bead, typically including $^{60}$Co or $^{192}$Ir, is inserted. The radioactive bead is typically connected by means of a wire to an afterloader that accurately controls the bead's position in the catheter. The bead is typically translated along the catheter in accordance with the therapy plan such that it remains in each of a number of predetermined positions, i.e. 'dwell positions', for a predetermined period, i.e. 'dwell time'. The treatment typically takes only a few minutes, following which the catheters are withdrawn and no radioactive material remains in the prostate.

An issue that affects prostate brachytherapy treatments in general, including LDR and HDR brachytherapy treatments, is that the prostate may change in position and size between the initial imaging procedure when the treatment planning image is generated, and the subsequent treatment-delivery phase, i.e. when the intra-treatment image(s) are generated. Changes in prostate position and size may for example be caused by the progression of the cancer, the swelling of the prostate, changes in the filling of the nearby bladder, or the presence of an endo-rectal, i.e. trans-rectal ultrasound 'TRUS', probe that is typically used to generate intra-treatment ultrasound images.

In one solution to this problem, document WO/2016/092463 discloses a system for dynamic localization of medical instruments that includes an ultrasound imaging system configured to image a volume where one or more medical instruments are deployed. A registration module registers two images of the one or more medical instruments to compute a transform between the two images, the two images being separated in time. A planning module is configured to have positions of the volume and the one or more medical instruments updated based on the transform and, in turn, update a treatment plan in accordance with the updated positions such that changes in the volume and positions of the one or more medical instruments are accounted for in the updated plan.

In spite of such developments there remains room to improve treatment planning for brachytherapy-based prostate treatments.

SUMMARY OF THE INVENTION

The present invention seeks to improve treatment planning for brachytherapy-based prostate treatments. Thereto a brachytherapy treatment planning system and an associated method and computer program product are provided. The brachytherapy treatment planning system includes a processor configured to:

receive a planning image corresponding to at least a portion of a prostate;

generate a brachytherapy treatment plan comprising, for each of a plurality of brachytherapy seeds or catheters, a corresponding brachytherapy seed or catheter position in the planning image such that the plurality of brachytherapy seed or catheter positions in the planning image together satisfy a desired radioactive dose objective in the prostate;

receive a pre-treatment image corresponding to the at least a portion of a prostate, the pre-treatment image being generated later in time to the planning image and earlier in time than the insertion of any brachytherapy seed or catheter into the prostate; and to map each brachytherapy seed or catheter position in the planning image to a corresponding position in the pre-treatment image by performing a registration between the planning image and the pre-treatment image.

During the time interval between the generation of the planning image and the pre-treatment image, various factors may affect the size, shape, and positioning of the prostate. These can include the progression of the cancer, the filling of the bladder, or the presence of a TRUS probe to generate intra-treatment images. The system provides that catheters that might be mis-positioned as a result of such factors become apparent to a user of the system. The user may subsequently decide to adapt part of the plan, or to generate an entirely new plan altogether. Advantageously since the pre-treatment image is generated earlier in time than the insertion of any brachytherapy seed or catheter into the prostate, the risk of such a mis-positioned brachytherapy seed or catheter intercepting an organ at risk is minimized. Treatment efficacy is thereby improved.

In accordance with one aspect the planning image and the pre-treatment image each include a corresponding organ at risk, and the processor of the system is further configured to:
  display the pre-treatment image including the organ at risk;
  indicate, in the pre-treatment image, each brachytherapy seed or catheter position; and to either:
    a) identify, in the pre-treatment image, at least one brachytherapy seed or catheter position that intercepts the organ at risk, or b) indicate, in the pre-treatment image that no brachytherapy seed or catheter position intercepts the organ at risk.

Advantageously this identification alerts the user to the consequence of delivering the current brachytherapy treatment plan.

In accordance with one aspect the processor of the system is further configured to:
  generate a revised brachytherapy treatment plan comprising, for each of the plurality of brachytherapy seeds or catheters, a corresponding revised brachytherapy seed or catheter position in the pre-treatment image such that the plurality of revised brachytherapy seed or catheter positions in the pre-treatment image together satisfy the desired radioactive dose objective in the prostate.

Advantageously since the revised brachytherapy treatment plan is made using the pre-treatment image it takes account of the up-to-date anatomy of the patient.

In accordance with one aspect the planning image and the pre-treatment image each include a corresponding organ at risk. Moreover, each of the plurality of brachytherapy seeds or catheters includes a corresponding insertion trajectory in the planning image. The processor of the system is further configured to:
  map each insertion trajectory in the planning image to a corresponding insertion trajectory in the pre-treatment image using the registration between the planning image and the pre-treatment image.

Advantageously this aspect provides that any catheter trajectory(ies) that might intercept an organ at risk as a result of factors such as changes in shape or position of the prostate, become apparent to a user of the system. Treatment efficacy is thereby improved. The user may subsequently decide to adapt part of the plan, or to generate an entirely new plan altogether.

Further aspects are described with reference to the appended claims.

Further advantages from the described invention will also be apparent to the skilled person.

DETAILED DESCRIPTION OF THE INVENTION

Prior to a brachytherapy procedure a patient typically undergoes an imaging procedure, for example MRI or computed tomography, i.e. CT, to determine the exact shape and size of the prostate. The planning image that results from this procedure is delineated or 'contoured' in order to identify the prostate and nearby critical organs. Imaging modalities such as MRI and CT are preferred for the generation of this image in view of their high resolution imaging capability. A treatment plan is subsequently generated from the planning image. For LDR brachytherapy this includes, for each of a number of brachytherapy seeds, a corresponding brachytherapy seed position in the planning image. For HDR brachytherapy the treatment plan includes, for each of a number of brachytherapy catheters, a corresponding brachytherapy catheter position in the planning image such that the plurality of brachytherapy catheter positions in the planning image together satisfy a desired radioactive dose objective in the prostate. Typically the brachytherapy seed or catheter positions in the planning image together satisfy multiple such dose objectives. The dose objectives may for example include the delivery of sufficient radiation dose to the cancerous regions in the prostate, the minimization of the radiation dose to critical structure(s) such as 'organs at risk', and the sparing of as much of the healthy nearby tissue as possible.

Figure 1:
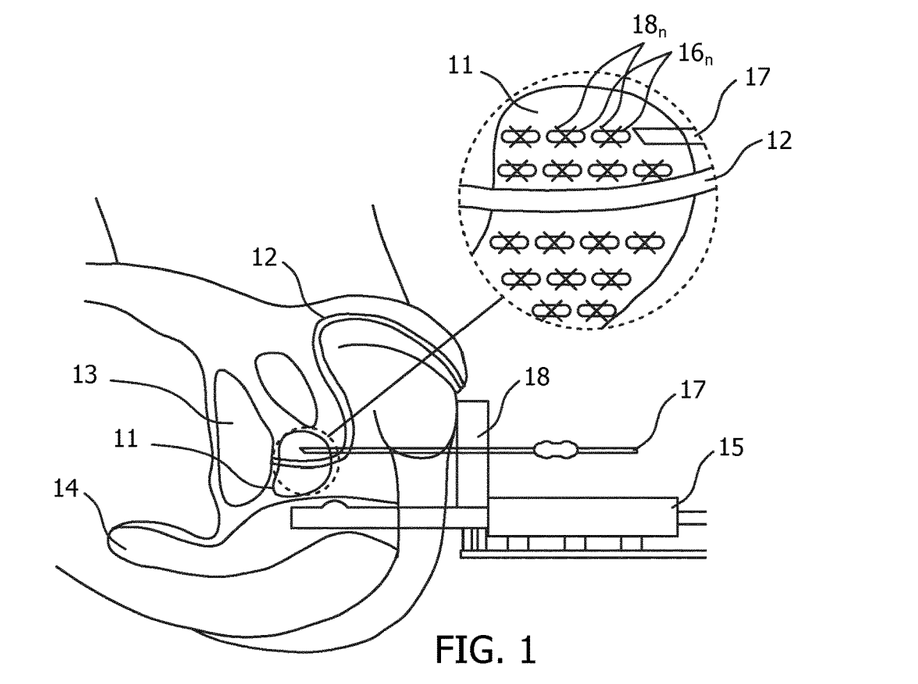
FIG. 1 illustrates an LDR brachytherapy procedure during which radioactive seeds are permanently positioned in the prostate.

In order to illustrate the principles of the present invention, FIG. 1 illustrates an LDR brachytherapy procedure during which radioactive seeds are permanently positioned in the prostate. It is however to be appreciated that the invention also finds application in other types of brachytherapy treatment planning, including the HDR brachytherapy procedure illustrated in FIG. 2.

With reference to FIG. 1, during an LDR brachytherapy treatment delivery procedure, brachytherapy seeds are implanted into the prostate in accordance with the treatment plan. Typically around 100 radioactive seeds that include radioactive iodine ($^{125}$I) are implanted in the patient under general anesthetic. In FIG. 1 various parts of the male anatomy are illustrated, including prostate 11, urethra 12, bladder 13 and rectum 14. Detail of prostate 11 within the dashed circle is shown in the cutout portion. An ultrasound imaging probe exemplified by TRUS imaging probe 15 is typically inserted into rectum 14 in order to guide the placement of radioactive seeds $16_n$ into prostate 11 by catheter 17. Catheter 17 is typically inserted to its maximum extent and then withdrawn whilst releasing seeds $16n$ in their desired positions $18n$. Care must be taken during the insertion of catheter 17 to avoid critical structures such as urethra 12, bladder 13, and the wall of rectum 14. To minimize this risk, TRUS imaging probe 15 is conventionally operated in a live imaging mode to generate live 'intra-treatment' images during the implantation procedure and thereby verify the positioning of the needles and the seeds respective the anatomy. A mechanical grid-like device, template 18 is typically fixably mounted to TRUS imaging probe 15 in order to guide the release of seeds 16n by catheter 17. This ensures that the seeds are inserted in predetermined positions respective the live ultrasound image. The depth of catheter 17 and the release of seeds 16n may be controlled manually by an operator in accordance with markings on the side of catheter 17, or instead its depth and the release of seeds 16n may be computer-controlled using a mechanical stepper device. In so doing, seeds 16n are inserted in accordance with their desired positions as defined in the planning image. It is to be noted that whilst a single catheter 17 is illustrated in FIG. 1, typically some 20-30 such catheters are used in a single procedure, each catheter implanting between 2 and 6 seeds.

An HDR brachytherapy treatment planning phase typically shares the same initial MRI or CT imaging procedure as the above-described LDR procedure. The resulting treatment planning image, is then used to generate an HDR brachytherapy treatment plan. However, rather than defining the positions of brachytherapy seeds, an HDR brachytherapy treatment plan defines, for each of a number of brachytherapy catheters, a corresponding brachytherapy catheter position in the planning image such that the plurality of brachytherapy catheter positions in the planning image together satisfy a desired radioactive dose objective in the prostate. In view of their temporary positions, these HDR brachytherapy catheter positions are typically termed 'dwell positions', the temporary radiation source, or bead, being maintained in each dwell position for a corresponding period referred-to as a 'dwell time'.

Figure 2:
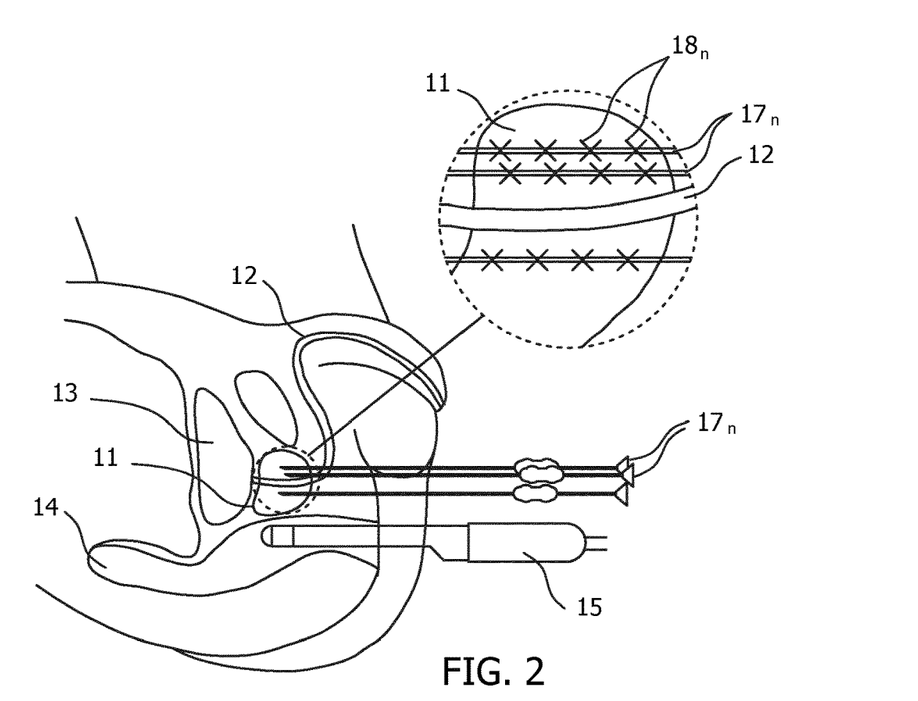
FIG. 2 illustrates an HDR brachytherapy procedure during which radioactive beads are temporarily positioned in the prostate by means of catheters.

The treatment delivery phase for HDR brachytherapy is however somewhat different to that in LDR brachytherapy. Thereto, FIG. 2 illustrates an HDR brachytherapy procedure during which radioactive beads are temporarily positioned in the prostate by means of catheters. Similarly-identified items in FIG. 2 refer to the same item in FIG. 1. With reference to FIG. 2, during an HDR brachytherapy treatment delivery procedure, an ultrasound imaging probe exemplified by TRUS imaging probe 15 is typically inserted into rectum 14 in order to guide the placement of catheters 17n into prostate 11. Catheters 17n are typically formed from plastic, and the position of a radioactive bead within each catheter is controlled by an afterloader by means of a wire. Some 15 to 20 catheters 17n are typically inserted into the prostate in a procedure. The radioactive bead typically includes $^{60}$Co or $^{192}$Ir. The afterloader, wire and bead are not shown in FIG. 2. Each bead is translated along its catheter 17n in accordance with the therapy plan such that it remains in each position 18n defined in the planning image, i.e. each dwell position, for a predetermined time, i.e. a dwell time. As in LDR brachytherapy, care must be taken during the insertion of catheter 17 to avoid critical structures such as urethra 12, bladder 13, and the wall of rectum 14. TRUS imaging probe 15 may therefore be used in a live imaging mode to generate live 'intra-treatment' images during the implantation procedure in order to verify the positioning of the needles and the seeds respective the anatomy. Although not shown in FIG. 2, a template similar to template 18 may be fixably mounted to TRUS imaging probe 15 in order to guide the insertion of catheters 17n.

Figure 3:
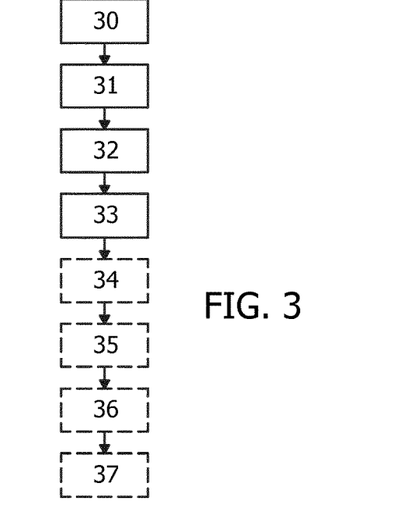
FIG. 3 illustrates various method steps that may be carried out in accordance with some aspects of the invention

FIG. 3 illustrates various method steps that may be carried out in accordance with some aspects of the invention. Whilst described in relation to LDR brachytherapy treatment planning, the method steps are also applicable to HDR brachytherapy treatment planning, and to brachytherapy treatment planning in general. In one embodiment the method described with reference to FIG. 3 may be carried out by the processor of a brachytherapy treatment planning system. Moreover, whilst illustrated as a sequential series of steps, some of these steps may be carried out in parallel or in a different order to that illustrated. The method steps disclosed herein may be recorded in the form of instructions which when executed on the processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

Returning to FIG. 3, and with additional reference to FIG. 1 and FIG. 2, in accordance with the present invention the brachytherapy treatment planning system includes a processor configured to:
receive 30 planning image 40 corresponding to at least a portion of a prostate 11;
generate 31 brachytherapy treatment plan 41 comprising, for each of a plurality of brachytherapy seeds 16n or catheters 17n, corresponding brachytherapy seed or catheter position 18n in planning image 40 such that the plurality of brachytherapy seed or catheter positions 18n in planning image 40 together satisfy a desired radioactive dose objective in the prostate 11;
receive 32 pre-treatment image 42 corresponding to the at least a portion of a prostate 11, pre-treatment image 42 being generated later in time to planning image 40 and earlier in time than the insertion of any brachytherapy seed or catheter into the prostate; and to
map 33 each brachytherapy seed or catheter position 18n in the planning image 40 to a corresponding position in the pre-treatment image 42 by performing a registration 43 between the planning image 40 and the pre-treatment image 42.

Figure 4:
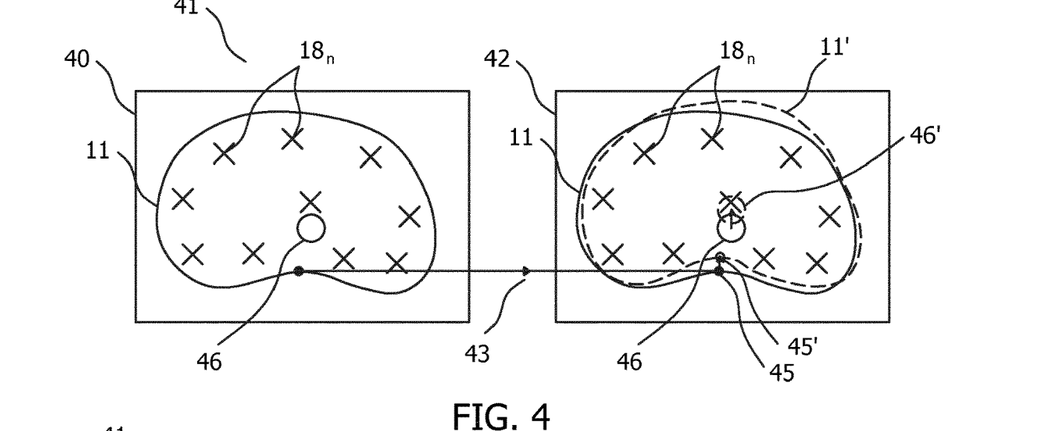
FIG. 4 illustrates the mapping of brachytherapy seed or catheter positions in a planning image to corresponding positions in a pre-treatment image based on a registration between the planning image and the pre-treatment image.

Planning image 40 may for example be an MRI, a CT or an ultrasound image that includes the prostate of the patient. The ultrasound image may for example be generated using a TRUS probe. MRI and CT images are preferred in view of their relatively higher resolution than ultrasound images and therefore their improved ability to distinguish different anatomical regions.

Pre-treatment image 42 may likewise be an MRI, a CT or an ultrasound image that includes the prostate of the patient. However, for pre-treatment image 42 an ultrasound image such as a TRUS image is preferred in view of optimizing workflow and minimizing X-ray radiation dose to the patient; sufficient anatomical detail generally being available from this relatively lower resolution imaging modality. Whereas planning image 40 is typically generated some days in advance of the delivery of the brachytherapy treatment in order to give sufficient time to generate and validate the brachytherapy treatment plan, pre-treatment image 42 is typically generated on the day of treatment, immediately prior to the insertion of any radioactive seeds or catheters into the prostate.

In one exemplary implementation, radiation therapy plan 41 may be generated form the planning image in accordance with the principles disclosed in document "Recent developments and best practice in brachytherapy treatment planning", C. D. Lee, Br. J. Radiol. September 2014; 87(1041). In one exemplary implementation, dose calculations may be computed using Monte Carlo simulations in accordance with the principles disclosed in document "Current state of the art brachytherapy treatment planning dosimetry algorithms", Papagiannis, P, et al., Br J Radiol. September 2014; 87(1041).

Registration 43 between planning image 40 and pre-treatment image 42 that is used in mapping 18 is preferably a rigid registration. In order to perform this registration, contours in one or both of the images may be delineated either a manual or an automatic segmentation technique. A combination of manual and automatic techniques may also be used. Automatic segmentation automatic segmentation techniques such as model-based segmentation technique, or registering the image to an anatomical atlas that includes the at least a portion of a prostate may for example be used. Following the contouring process, points on the contours, or the contours themselves may be matched using a rigid registration, i.e. transformation that in a least squares sense, best matches the two images. A contour-based registration 43 is illustrated on the right side of FIG. 4 in which a contour of prostate 11 from planning image 40 is overlaid on a corresponding, dashed, contour of prostate 11' from pre-treatment image 42. Alternatively the rigid registration process may be used in the absence of contouring, wherein points, or landmarks, on each of the two images may likewise be matched using a rigid registration, i.e. transformation that in a least squares sense, best matches the two images. Such a landmark-based registration is illustrated on the right side of FIG. 4 in which landmark 45 of prostate 11 from planning image 40 is best-matched to corresponding landmark 45' in pre-treatment image 42.

In one implementation the above-described contouring or segmentation is performed on planning image 40, and features of the pre-treatment image including the prostate are segmented by non-rigidly registering the so-segmented planning image 40 to the pre-treatment image 42. This implementation may have the benefit of reducing segmentation time and/or improving segmentation accuracy, particularly when the planning image has relatively higher resolution than the pre-treatment image.

Registration 43 ultimately defines a vector that is used in mapping each brachytherapy seed or catheter position 18$n$ in the planning image 40 to a corresponding position in the pre-treatment image 42. However, in FIG. 4, the position of urethra 46, as an example of an organ at risk, is shifted upwards to position 46' in dash-contoured pre-treatment image 42 respective solid-contoured planning image 40. This shift may for example be caused by pressure on prostate 11 following the insertion of TRUS imaging probe 15. The nearby brachytherapy seed position that is mapped into pre-treatment image 42 now intercepts urethra 46. Mapping 33 therefore serves to warn a user of the brachytherapy planning system that should the brachytherapy seeds be inserted in accordance with the current brachytherapy plan, urethra 46' could be harmed.

Optionally, and with reference to FIG. 3, the processor may be further configured to:
- display 34 pre-treatment image 42 including organ at risk 46;
- indicate 35, in pre-treatment image 42, each brachytherapy seed or catheter position 18$n$; and to either
  - a) identify 36, in pre-treatment image 42, at least one brachytherapy seed or catheter position that intercepts organ at risk 46, or b) indicate, in the pre-treatment image 42 that no brachytherapy seed or catheter position intercepts the organ at risk 46.

In so doing the risk of delivering the current brachytherapy treatment plan may be indicated to a user of the system. The identification may for example include changing the shape, color, saturation or hue of a marker corresponding to the relevant brachytherapy seed or catheter position 18$n$ in pre-treatment image 42, highlighting said marker, causing said marker to flash intermittently, or indicating in text form the relevant intercepting position 18$n$. By alternatively indicating that no brachytherapy seed or catheter position intercepts organ at risk 46 a user of the system may readily achieve confidence in the current brachytherapy treatment plan. Such identification or indication may be achieved by comparing the two or three dimensional positions of the brachytherapy seed(s) or catheter(s) respective the organ at risk. The indication that no brachytherapy seed or catheter position intercepts the organ at risk may for example be in the form of e.g. displayed text, or as described above, by changing the shape, color, saturation or hue of representative markers.

Optionally, and with continued reference to FIG. 3, the processor may be further configured to:
- generate 37 a revised brachytherapy treatment plan comprising, for each of the plurality of brachytherapy seeds 16$n$ or catheters 17$n$, a corresponding revised brachytherapy seed or catheter position in pre-treatment image 42 such that the plurality of revised brachytherapy seed or catheter positions in pre-treatment image 42 together satisfy the desired radioactive dose objective in the prostate 11.

In this latter step, since the revised brachytherapy treatment plan is made for pre-treatment image 42 it takes account of the up-to-date positions and shaped of the prostate and any organ(s) at risk. A more effective brachytherapy treatment plan may therefore be delivered. The revised brachytherapy treatment plan can be computed using for example the above-mentioned Monte Carlo dose simulations. In one implementation any brachytherapy seed or catheter positions that are not identified as intercepting the organ at risk are maintained in their original positions in pre-treatment image 42 and only brachytherapy seed or catheter positions that are identified as intercepting the organ at risk 46 are adjusted in the pre-treatment image. Brachytherapy seed or catheter positions that are identified as intercepting the organ at risk 46 may be adjusted to a new position in the pre-treatment image, or removed entirely. This implementation has the benefit of a faster re-planning time. In another implementation the revised brachytherapy treatment plan may involve adding one or more new brachytherapy seeds or catheters to the plurality of brachytherapy seeds 16$n$ or catheters 17$n$. Each new brachytherapy seed or catheter has a corresponding added brachytherapy seed or catheter position in pre-treatment image 42, such that the plurality of revised brachytherapy seed or catheter positions including the added brachytherapy seed or catheter positions in the pre-treatment image 42 together satisfy the desired radioactive dose objective in the prostate 11. In this implementation the added positions can be used to deliver a dose that accurately meets the desired radioactive dose objective in the prostate 11.

Figure 5:
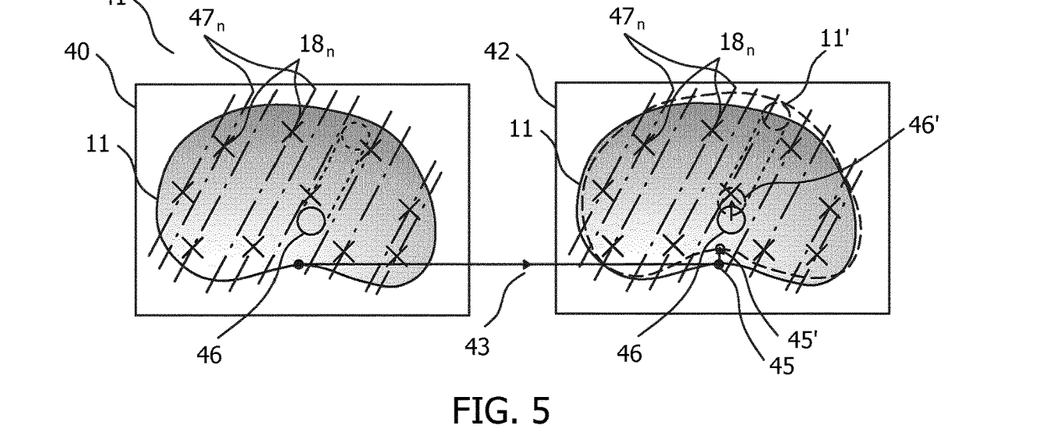
FIG. 5 illustrates the mapping of brachytherapy seed or catheter insertion trajectories in a planning image to corresponding trajectories in a pre-treatment image based on the registration between the planning image and the pre-treatment image.

In another implementation each of the plurality of brachytherapy seeds 16$n$ or catheters 17$n$ includes a corresponding insertion trajectory 47$n$ in planning image 40. Thereto, FIG. 5 illustrates the mapping of brachytherapy seed or catheter insertion trajectories in a planning image to corresponding trajectories in a pre-treatment image based on the registration 43 between the planning image and the pre-treatment image. Items in FIG. 5 that correspond to the same items in FIG. 4 are identified with the same labels. Planning image 40 and pre-treatment image 42 are illustrated as three-dimensional images in FIG. 5, although these may alternatively be two-dimensional image slices as illustrated in FIG. 4. With reference to FIG. 5, planning image 40 and pre-treatment image 42 optionally each include urethra 46, as an example of an organ at risk. In this implementation, the processor is further configured to:

map each insertion trajectory 47$n$ in the planning image 40 to a corresponding insertion trajectory 47$n$ in pre-treatment image 42 using the registration 43 between the planning image 40 and pre-treatment image 42.

By mapping the trajectories a further warning is provided to a user of the brachytherapy planning system that should the brachytherapy seeds be inserted in accordance with the brachytherapy plan, the organ at risk, in this example urethra 46, could be harmed. As illustrated in FIG. 5 the deformation of the prostate results in an insertion trajectory that passes through the current position of the urethra.

In this implementation the processor may optionally be further configured to:

display pre-treatment image 42 including organ at risk 46;
    indicate, in pre-treatment image 42, each brachytherapy seed or catheter position 18$n$ and its corresponding insertion trajectory 47$n$; and to
    a) identify, in pre-treatment image 42, at least one brachytherapy seed or catheter position that intercepts the organ at risk 46 and/or identify, in pre-treatment image 42, at least one insertion trajectory 47$n$ that intercepts the organ at risk 46 or b) indicate, in the pre-treatment image (42) that no brachytherapy seed or catheter position intercepts the organ at risk (46) and/or indicate, in the pre-treatment image (42) that no insertion trajectory (42$n$) intercepts the organ at risk (46).

In so doing, a more robust warning is provided to the user, particularly when image slices are displayed and the interception of the organ at risk occurs in an image slice that is not currently displayed. In the alternative, by indicating that no brachytherapy seed or catheter position intercepts organ at risk 46, or that no insertion trajectory (42$n$) intercepts the organ at risk (46) a user of the system may readily achieve confidence in the current brachytherapy treatment plan. Such identification or indication may be achieved by comparing the two or three dimensional positions of the brachytherapy seed(s) or catheter(s) respective the organ at risk In this implementation the processor may optionally be further configured to identify, in pre-treatment image 42, at least one insertion trajectory 47$n$ that intercepts the organ at risk 46, and to:

adjust, in pre-treatment image 42, the at least one identified insertion trajectory such that it does not intercept the organ at risk 46.

This step can be carried out by either adjusting the respective brachytherapy seed or catheter position 18$n$, or without adjusting its position, and thereby only adjusting its trajectory. The latter possibility is simpler in that no dose re-computation is required. If necessary, re-positioning of the catheter can be carried out using for example the above-mentioned Monte Carlo dose simulations.

It is to be noted that whilst the above-mentioned method steps are described as being carried out by a processor of a brachytherapy treatment planning system, the method steps may alternatively be recorded in the form of instructions which when executed on a processor cause the processor to carry out such method steps. Moreover, the steps need not necessarily be carried out in the order described, and they may be combined with other steps described herein to obtain further advantageous effects.

In summary, a brachytherapy treatment planning system has been described in which a processor of the system receives a planning image corresponding to at least a portion of a prostate; generates a brachytherapy treatment plan comprising, for each of a plurality of brachytherapy seeds or catheters, a corresponding brachytherapy seed or catheter position in the planning image such that the plurality of brachytherapy seed or catheter positions in the planning image together satisfy a desired radioactive dose objective in the prostate; receives a pre-treatment image corresponding to the at least a portion of a prostate, the pre-treatment image being generated later in time to the planning image and earlier in time than the insertion of any brachytherapy seed or catheter into the prostate; and maps each brachytherapy seed or catheter position in the planning image to a corresponding position in the pre-treatment image by performing a registration between the planning image and the pre-treatment image.

The invention claimed is:

1. A brachytherapy treatment planning system; the system comprising a processor configured to:
    receive a planning image corresponding to at least a portion of a prostate;
    generate a brachytherapy treatment plan comprising, for each of a plurality of brachytherapy seeds or catheters, a corresponding brachytherapy seed or catheter position in the planning image such that the plurality of brachytherapy seed or catheter positions in the planning image together satisfy a desired radioactive dose objective in the prostate;
    receive a pre-treatment image corresponding to the at least a portion of a prostate, the pre-treatment image being generated later in time to the planning image and earlier in time than the insertion of any brachytherapy seed or catheter into the prostate; and to map each brachytherapy seed or catheter position in the planning image to a corresponding position in the pre-treatment image by performing a registration between the planning image and the pre-treatment image, wherein the registration defines a vector for use in mapping each brachytherapy seed or catheter position in the planning image to the corresponding position in the pre-treatment image, wherein the planning image and the pre-treatment image each include a corresponding organ at risk, and further wherein the mapping in the pre-treatment image of one or more brachytherapy seed or catheter position may intercept the organ at risk, whereby the mapping is adapted to warn a user of the brachytherapy treatment planning system that should the brachytherapy seeds or catheters be inserted in accordance with the generated brachytherapy treatment plan, the organ at risk could be harmed.

2. The system according to claim 1, wherein the processor is further configured to:
display the pre-treatment image including the organ at risk;
indicate, in the pre-treatment image, each brachytherapy seed or catheter position; and to either:
a) identify, in the pre-treatment image, at least one brachytherapy seed or catheter position that intercepts the organ at risk, or b) indicate, in the pre-treatment image that no brachytherapy seed or catheter position intercepts the organ at risk.

3. The system according to claim 2, wherein the processor is further configured to:
generate a revised brachytherapy treatment plan comprising, for each of the plurality of brachytherapy seeds or catheters, a corresponding revised brachytherapy seed or catheter position in the pre-treatment image such that the plurality of revised brachytherapy seed or catheter positions in the pre-treatment image together satisfy the desired radioactive dose objective in the prostate.

4. The system according to claim 3, wherein generating the revised brachytherapy treatment plan comprises: for each brachytherapy seed or catheter position that is not identified as intercepting the organ at risk, maintaining its position in the pre-treatment image; and for each brachytherapy seed or catheter position that is identified as intercepting the organ at risk, adjusting its position in the pre-treatment image.

5. The system according to claim 3, wherein generating the revised brachytherapy treatment plan comprises adding one or more new brachytherapy seeds or catheters to the plurality of brachytherapy seeds or catheters, each new brachytherapy seed or catheter having a corresponding added brachytherapy seed or catheter position in the pre-treatment image, such that the plurality of revised brachytherapy seed or catheter positions including the added brachytherapy seed or catheter positions in the pre-treatment image together satisfy the desired radioactive dose objective in the prostate.

6. The system according to claim 1, wherein each of the plurality of brachytherapy seeds or catheters includes a corresponding insertion trajectory in the planning image, and wherein the processor is further configured to:
map each insertion trajectory in the planning image to a corresponding insertion trajectory in the pre-treatment image using the registration between the planning image and the pre-treatment image.

7. The system according to claim 6, being wherein the processor is further configured to:
display the pre-treatment image including the organ at risk;
indicate, in the pre-treatment image, each brachytherapy seed or catheter position and its corresponding insertion trajectory; and to either:
a) identify, in the pre-treatment image, at least one brachytherapy seed or catheter position that intercepts the organ at risk and/or identify, in the pre-treatment image, at least one insertion trajectory that intercepts the organ at risk, or b) indicate, in the pre-treatment image that no brachytherapy seed or catheter position intercepts the organ at risk and/or indicate, in the pre-treatment image that no insertion trajectory intercepts the organ at risk.

8. The system according to claim 7, wherein the processor is configured to identify, in the pre-treatment image, at least one insertion trajectory that intercepts the organ at risk, and wherein the system is further configured to:
adjust, in the pre-treatment image, the at least one identified insertion trajectory such that it does not intercept the organ at risk.

9. The system according to claim 8, wherein the adjusting is performed without adjusting the corresponding brachytherapy seed or catheter position.

10. The system according to claim 1, wherein the processor is further configured to segment the at least a portion of a prostate in the planning image and/or in the pre-treatment image by either i) using a model-based segmentation technique, or by ii) registering the planning image and/or the pre-treatment image to an anatomical atlas that includes the at least a portion of a prostate.

11. The system according to claim 1, wherein the processor is further configured to segment the organ at risk in the planning image and/or the pre-treatment image using either a model-based segmentation technique, or by registering the planning image and/or the pre-treatment image to an anatomical atlas that includes the organ at risk.

12. The system according to claim 1, wherein the processor is further configured to segment the at least a portion of a prostate and the organ at risk in the planning image using either a model-based segmentation technique, or by registering the planning image to an anatomical atlas that includes the at least a portion of a prostate and the organ at risk; and to
segment the at least a portion of a prostate and the organ at risk in the pre-treatment image by performing a non-rigid registration between the planning image and the pre-treatment image.

13. The system according to claim 1, wherein the planning image is an X-ray image, or a CT image, or an MRI image and/or wherein the pre-treatment image is an ultrasound image.

14. The system according to claim 1, wherein the registration between the planning image and the pre-treatment image comprises one of a rigid registration and a non-rigid registration, wherein the rigid registration includes one of (i) contour-based registration in which points on contours delineated in one or both images, or the contours themselves, are matched via a transformation that in a least squares sense, best matches the planning image and the pre-treatment image, (ii) landmark-based registration in which points, or landmarks, on each of the two images are matched via a transformation that in a least squares sense, best matches the planning image and the pre-treatment image, and wherein the non-rigid registration includes (a) performing contouring or segmentation on the planning image and (b) segmenting features of the pre-treatment image by non-rigidly registering the contoured or segmented planning image to the pre-treatment image.

15. Brachytherapy treatment planning method; the method comprising the steps of:
receiving a planning image corresponding to at least a portion of a prostate;
generating a brachytherapy treatment plan comprising, for each of a plurality of brachytherapy seeds or catheters, a corresponding brachytherapy seed or catheter position in the planning image such that the plurality of brachytherapy seed or catheter positions in the planning image together satisfy a desired radioactive dose objective in the prostate;
receiving a pre-treatment image corresponding to the at least a portion of a prostate, the pre-treatment image being generated later in time to the planning image and earlier in time than the insertion of any brachytherapy seed or catheter into the prostate;
mapping each brachytherapy seed or catheter position in the planning image to a corresponding position in the pre-treatment image by performing a registration between the planning image and the pre-treatment image, wherein the registration defines a vector for use in mapping each brachytherapy seed or catheter position in the planning image to the corresponding position in the pre-treatment image, wherein the planning image and the pre-treatment image each include a corresponding organ at risk, and further wherein the mapping in the pre-treatment image of one or more brachytherapy seed or catheter position may intercept the organ at risk, whereby the mapping is adapted to warn a user of the brachytherapy treatment planning that should the brachytherapy seeds or catheters be inserted in accordance with the generated brachytherapy treatment plan, the organ at risk could be harmed.

16. The method according to claim 15, further comprising the steps of:
displaying the pre-treatment image including the organ at risk;
indicating, in the pre-treatment image, each brachytherapy seed or catheter position; and to either:
a) identify, in the pre-treatment image, at least one brachytherapy seed or catheter position that intercepts the organ at risk, or b) indicate, in the pre-treatment image that no brachytherapy seed or catheter position intercepts the organ at risk.

17. The method according to claim 15, wherein each of the plurality of brachytherapy seeds or catheters includes a corresponding insertion trajectory in the planning image, the method further comprising the steps of:
mapping each insertion trajectory in the planning image to a corresponding insertion trajectory in the pre-treatment image using the registration between the planning image and the pre-treatment image.

18. The method according to claim 15, further comprising the steps of:
segmenting the at least a portion of a prostate in the planning image and/or in the pre-treatment image by either i) using a model-based segmentation technique, or by ii) registering the planning image and/or the pre-treatment image to an anatomical atlas that includes the at least a portion of a prostate.

19. The method according to claim 15, wherein the planning image is an X-ray image, or a CT image, or an MRI image and/or wherein the pre-treatment image is an ultrasound image.

20. A non-transitory computer program product comprising instructions which when executed on a processor cause the processor to carry out the method steps of claim 15.

* * * * *